United States Patent [19]

Sato et al.

[11] Patent Number: 4,760,150  
[45] Date of Patent: Jul. 26, 1988

[54] BIS(METHYLENEDIOXYPHENYL-)IMIDAZOLES

[75] Inventors: Shinichi Sato, Koriyama; Hideyuki Sensui, Tokyo; Hiroto Takita, Koriyama, all of Japan

[73] Assignee: Hodogaya Chemical Co., Ltd., Tokyo, Japan

[21] Appl. No.: 43,448

[22] Filed: Apr. 28, 1987

[30] Foreign Application Priority Data

Apr. 28, 1986 [JP] Japan ............................... 61-096630

[51] Int. Cl.$^4$ ........................................ C07D 405/14
[52] U.S. Cl. .................................................. 548/336
[58] Field of Search ...................................... 548/336

[56] References Cited

U.S. PATENT DOCUMENTS 3,784,557  1/1974  Cescon .................................. 548/336
4,188,397  2/1980  Hill ........................................ 548/336 X
4,460,598  7/1984  Lautenschlaeger ............. 548/336 X

FOREIGN PATENT DOCUMENTS 448730  4/1968  Switzerland ........................ 548/336

OTHER PUBLICATIONS

*Chemical Abstracts*, 74:125654a (1971)[Maeda, K., et al., *Bull. Chem. Soc. Jap.* 1971, 44(2), 533–6].

*Primary Examiner*—Richard A. Schwartz  
*Attorney, Agent, or Firm*—Oblon, Fisher, Spivak, McClelland & Maier

[57] ABSTRACT

A 2,4-5-triphenylimidazole compound having the formula:

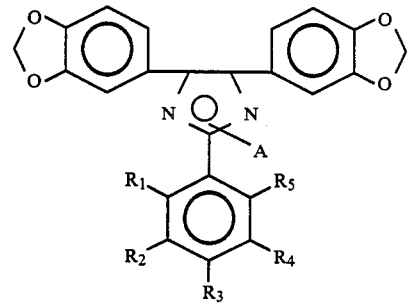

wherein each of $R_1$ to $R_5$ is a hydrogen atom, a $C_1$–$C_4$ alkyl group, a $C_1$–$C_4$ alkoxy group, a fluorine atom, a chlorine atom, a bromine atom, a trifluoromethyl group or a trichloromethyl group, and A is a group having the formula:

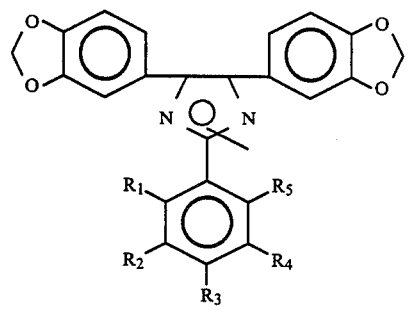

wherein $R_1$ and $R_5$ are as defined above.

These compounds are useful as chlorine sources for photographic image-forming compositions, and as intermediates for dimers of 2,4-5-triphenylimidazoles which are useful as photochromic agents in sunglasses.

8 Claims, No Drawings

BIS(METHYLENEDIOXYPHENYL)IMIDAZOLES

The present invention relates to novel 2,4,5-triphenylimidazole compounds. More particularly, it relates to novel 2,4,5-triphenylimidazoles and dimers thereof. The 2,4,5-triphenylimidazoles of the present invention are useful as chlorine sources for photographic image-forming compositions, as intermediates for pharmaceuticals or agricultural chemicals, or as intermediates for dimers of 2,4,5-triphenylimidazoles. The dimers of 2,4,5-triphenylimidazoles have a photochromic property and they are useful as radical-forming agents or as photo-oxidizing agents for photo-resists, PS plates or proofing materials, or as photochromic agents for sun glasses or window glasses.

2,4,5,-triphenylimidazoles can be prepared in accordance with J. Org. Chem. 2319 (1937). Their dimers can be prepared in accordance with BULLETIN OF THE CHEMICAL SOCIETY OF JAPAN, 33, 565 (1960). More specifically, as 2,4,5-triphenylimidazoles, 2-(2-chlorophenyl)-4,5-diphenyl-imdidazole and 2-(2-chlorophenyl)-4,5-bis(3-methoxyphenyl)-imidazole are well known. Likewise, as dimers of 2,4,5-triphenylimidazoles, dimers of 2-(2-chlorophenyl)-4,5-diphenyl-imidazole and 2-(2-chlorophenyl)-4,5-bis(3-methoxyphenyl)-imidazole are well known.

It is an object of the present invention to provide a novel 2,4,5-triphenylimidazole and a dimer thereof.

The present invention provides a novel 2,4,5-triphenylimidazole compound having the formula:

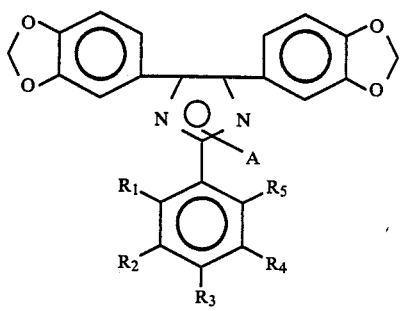

(I)

wherein each of $R_1$ to $R_5$ is a hydrogen atom, a $C_1$–$C_4$ alkyl group, a $C_1$–$C_4$ alkoxy group, a fluorine atom, a chlorine atom, a bromine atom, a trifluoromethyl group or a trichloromethyl group, and A is a hydrogen atom or a group having the formula:

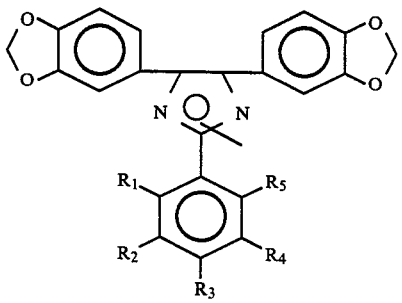

(II)

wherein $R_1$ to $R_5$ are as defined above.

Namely, the compound of the present invention includes a compound of the formula I wherein A is a hydrogen atom and a dimer thereof i.e. a compound of the formula I wherein A is a group of the formula II.

Now, the present invention will be described in detail with reference to the preferred embodiments.

Specific examples of the imidazole compound of the formula I of the present invention, include 2-phenyl-4,5-bis(3,4-methylenedioxyphenyl)-imidazole, 2-(2-chlorophenyl)-4,5-bis(3,4-methylenedioxyphenyl)-imidazole, 2-(3-chlorophenyl)-4,5-bis(3,4-methylenedioxyphenyl)-imidazole, 2-(4-chlorophenyl)-4,5-bis(3,4-methylenedioxyphenyl)-imidazole, 2-(2-bromophenyl)-4,5-bis(3,4-methylenedioxyphenyl)-imidazole, 2-(2-fluorophenyl)-4,5-bis(3,4-methylenedioxyphenyl)-imidazole, 2-(2,3-dichlorophenyl)-4,5-bis(3,4-methylenedioxyphenyl)-imidazole, 2-(2,4-dichlorophenyl)-4,5-bis(3,4-methylenedioxyphenyl)-imidazole, 2-(3,5-dichlorophenyl)-4,5-bis(3,4-methylenedioxyphenyl)-imidazole 2-(2,6-dichlorophenyl)-4,5-bis(3,4-methylenedioxyphenyl)-imidazole, 2-(2,3-dimethoxyphenyl)-4,5-bis(3,4-methylenedioxyphenyl)-imidazole, 2-(2,4-dimethoxyphenyl)-4,5-bis(3,4-methylenedioxyphenyl)-imidazole, 2-(2-chloro-5-methoxyphenyl)-4,5-bis(3,4-methylenedioxyphenyl)-imidazole, 2-(5-chloro-2-methoxyphenyl)-4,5-bis(3,4-methylenedioxyphenyl)-imidazole, 2-(2-trichloromethylphenyl)-4,5-bis(3,4-methylenedioxyphenyl)-imidazole, 2-(4-trichloromethylphenyl)-4,5-bis(3,4-methylenedioxyphenyl)-imidazole, 2-(2-trifluoromethylphenyl)-4,5-bis(3,4-methylenedioxyphenyl)-imidazole, 2-(4-trifluoromethylphenyl)-4,5-bis(3,4-methylenedioxyphenyl)-imidazole, and 2-(p-tolyl)-4,5-bis(3,4-methylenedioxyphenyl)-imidazole, and dimers thereof.

Now, the present invention will be described in further detail with reference to Examples. However, it should be understood that the present invention is by no means restricted to such specific Examples.

EXAMPLE 1

Preparation of 2-(2-chlorophenyl)-4,5-bis(3,4-methylenedioxyphenyl)-imidazole To a solution comprising 5.5 g (0.02 mol) of piperil, 58 g of glacial acetic acid and 7.7 g of ammonium acetate, 2.8 g (0.02 mol) of o-chlorobenzaldehyde was added, and the solution thus obtained was refluxed for 4 hours. Then, 100 ml of water was poured to the reaction solution, and the precipitates were collected by filtration. The solid thus obtained, was recrystallized from toluene to obtain 7.5 g of 2-(2-chlorophenyl)-4,5-bis(3,4-methylenedioxyphenyl)-imidazole (mp: 181.4°–182.3° C.).

Ths structure was confirmed by the following results of the elemental analysis.

|  | C | H | N | Cl |
| --- | --- | --- | --- | --- |
| Calculated (%) | 65.95 | 3.58 | 6.69 | 8.48 |
| Found (%) | 66.01 | 3.50 | 6.71 | 8.40 |

Preparation of a dimer 12.8 g of 10% sodium hydroxide, 6.6 g (0.02 mol) of potassium ferricyanide and 20 ml of benzene were charged, and 4.2 g (0.01 mol) of 2-(2-chlorophenyl)-4,5-bis(3,4-methylenedioxyphenyl)-imidazole was added thereto. The mixture was stirred at a temperature of from 75° to 80° C. for 3 hours. The benzene solution was concentrated, and the product was recrystallized from benzene to obtain 2.9 g of a dimer of 2-(2-chlorophenyl)-4,5-bis(3,4-methylenedioxyphenyl)-imidazole (mp: 168.0°-170.0° C.). The results of the elemental analysis and the NMR analysis of the dimer are shown below.

| | Elemental analysis | | | |
|---|---|---|---|---|
| | C | H | N | Cl |
| Calculated (%) | 66.11 | 3.35 | 6.71 | 8.50 |
| Found (%) | 65.99 | 3.33 | 6.75 | 8.44 |

$^{13}$C-NMR δ(CDCl$_3$): 100.7, 101.6, 107.5, 107.9, 109.8, 112.7, 120.9, 124.9, 125.1, 125.7, 126.2, 128.1, 128.9, 129.8, 131.0, 132.8, 134.4, 134.6, 135.0, 138.0, 143.7, 145.9, 146.8, 147.5, 147.7, 150.3, 164.9, 167.7.

This dimer was yellow crystals, and turned green when its 1% benzene solution was exposed to ultraviolet rays.

EXAMPLE 2

Preparation of 2-(2,3-dichlorophenyl)-4,5-bis(3,4-methylenedioxyphenyl)-imidazole In the same manner as in Example 1, 8.3 g of 2-(2,3-dichlorophenyl)-4,5-bis(3,4-methylenedioxyphenyl)-imidazole (mp: 197.5° C.) was obtained from 3.5 g of 2,3-dichlorobenzaldehyde and 5.5 g of piperil.

The results of the elemental analysis are shown below.

| | C | H | N | Cl |
|---|---|---|---|---|
| Calculated (%) | 60.93 | 3.09 | 6.18 | 15.67 |
| Found (%) | 61.11 | 3.01 | 6.11 | 15.72 |

Preparation of a dimer

In the same manner as in Example 1, 4.5 g of this imidazole compound was oxidized to obtain 3.6 g of a dimer of 2-(2,3-dichlorophenyl)-4,5-bis(3,4-methylenedioxyphenyl)-imidazole. This dimer was yellow crystals having a melting point of from 182.3° to 183.0° C. and had a photochromic property such that it turned green when exposed to sunlight.

| | Elemental analysis | | | |
|---|---|---|---|---|
| | C | H | N | Cl |
| Calculated (%) | 61.06 | 2.88 | 6.19 | 15.71 |
| Found (%) | 61.50 | 2.93 | 6.11 | 15.65 |

$^{13}$C-NMR δ(CDCl$_3$): 101.0, 101.6, 107.9, 109.7, 110.1, 120.9, 124.8, 125.3, 126.6, 129.4, 130.6, 130.9, 132.6, 137.2, 146.1, 147.2, 147.6, 150.5, 165.7, 168.0.

EXAMPLE 3

Preparation of 2-(2-trifluoromethylphenyl)-4,5-bis(3,4-methylenedioxyphenyl)-imidazole In the same manner as in Example 1, 8.1 g of 2-(2-trifluoromethylphenyl)-4,5-bis(3,4-methylenedioxyphenyl)-imidazole (mp: 230.5°-231.8° C.) was prepared from 3.5 g of o-trifluoromethylbenzaldehyde and 5.5 g of piperil.

| | Elemental analysis | | | |
|---|---|---|---|---|
| | C | H | N | Cl |
| Calculated (%) | 63.72 | 3.32 | 6.19 | 12.61 |
| Found (%) | 64.01 | 3.30 | 6.12 | 12.59 |

Preparation of a dimer 4.5 g of the triphenylimidazole prepared above, was oxidized in the same manner as in Example 1 to obtain 3.7 g of a dimer of 2-(2-trifluoromethylphenyl)-4,5-bis(3,4-methylenedioxyphenyl)-imidazole. This dimer had a melting point of 160.0° C., and had a photochromic property such that it turned from yellow to green.

| | Elemental analysis | | | |
|---|---|---|---|---|
| | C | H | N | Cl |
| Calculated (%) | 63.86 | 3.10 | 6.21 | 12.64 |
| Found (%) | 64.08 | 3.08 | 6.18 | 12.58 |

$^{13}$C-NMR δ(CDCl$_3$): 98.2, 100.6, 101.0, 101.6, 107.6, 107.9, 110.2, 112.9, 114.6, 120.6, 124.4, 125.3, 125.7, 126.2, 128.1, 130.3, 131.1, 132.2, 132.7, 133.3, 135.0, 137.6, 138.5, 142.8, 146.2, 146.4, 147.1, 150.2, 151.5, 165.1, 166.3, 168.1, 171.1, 190.0.

EXAMPLE 4

Preparation of 2-(2,4-dimethoxyphenyl)-4,5-bis(3,4-methylenedioxyphenyl)-imidazole In the same manner as in Example 1, 5.8 g of 2-(2,4-dimethoxyphenyl)-4,5-bis(3,4-methylenedioxyphenyl)-imidazole (mp: 123° C.) was prepared from 3.3 g of 2,4-dimethoxybenzaldehyde and 5.5 g of piperil. The structure was confirmed by the following results of the elemental analysis.

| | Elemental analysis | | |
|---|---|---|---|
| | C | H | N |
| Calculated (%) | 67.57 | 4.50 | 6.31 |
| Found (%) | 67.60 | 4.43 | 6.29 |

Preparation of a dimer 4.4 g of the triphenylimidazole prepared above, was oxidized in the same manner as in Example 1 to obtain 3.3 g of a dimer of 2-(2,4-dimethoxyphenyl)-4,5-bis(3,4-methylenedioxyphenyl)-imidazole. mp: 95.0° C.

This dimer showed photochromism such that the color changed from yellow to green upon exposure to ultraviolet rays.

The results of the elemental analysis and the NMR analysis of the dimer are shown below.

| | Elemental analysis | | |
|---|---|---|---|
| | C | H | N |
| Calculated (%) | 67.72 | 4.29 | 6.32 |
| Found (%) | 67.60 | 4.21 | 6.28 |

$^{13}$C-NMR δ(CDCl$_3$): 52.0, 55.5, 97.9, 98.7, 101.0, 101.6, 104.5, 105.7, 108.4, 111.4, 121.4, 124.2, 125.9, 127.7, 129.4, 134.6, 145.8, 146.7, 147.6, 149.8, 156.8, 160.9, 163.6, 166.4, 169.3, 188.3, 189.8, 192.8

Application Example 1

| Solution I (color-forming solution): | |
|---|---|
| Tris-(4-diethylamino-o-tolyl)methane | 0.8 part |
| 2-(2-Trifluoromethylphenyl)-4,5-bis(3,4-methylenedioxyphenyl)-imidazole dimer | 1.1 parts |
| Dodecylbenzene sulfonic acid | 1.1 parts |
| Polyethylene glycol (Average molecular weight: 1000) | 1.4 parts |
| Eslec C (manufactured by Sekisui Chemical Co., Ltd.) | 3.0 parts |
| Tetrahydrofuran | 30 parts |
| Ethanol | 6 parts |
| Solution II (fixing solution) | |
| 1,3-Diphenylguanidine | 0.41 part |
| Polyvinyl alcohol | 1.0 part |
| 70% Ethanol | 20 parts |

The above Solutions I and II were prepared separately. Then, Solution II was applied on a coating paper in an amount of 30 g/m² by means of a bar coater, and dried. Further, Solution I was applied thereon in an amount of 20 g/m² and dried. A step tablet No. 2 manufactured by Kodak Company was overlaid on the photosensitive sheet thus obtained, and exposure was conducted for 5 minutes in a vacuum exposure frame (P-113-B manufactured by Dai Nippon Screen Seizo K.K.) to obtain a blue color image. Then, the photosensitive sheet was heated at 100° C. for 5 minutes to obtain a permanent image which underwent no further color-development even when subjected to exposure again.

As a Comparative Example, a photosensitive sheet was prepared in the same manner as in Application Example 1 except that 1.08 parts of 2,2'-bis(2-chlorophenyl)-4,5,4',5'-tetraphenyl-1,2'-biimidazole was used instead of the 2-(2-trifluoromethylphenyl)-4,5-bis(3,4-methylenedioxyphenyl)-imidazole dimer, followed by the same treatment as in Application Example 1 to obtain a blue color image.

The results are shown in Table 1.

TABLE 1

| Example No. | Image* density | Fogging density | γ-value | Sensitivity $D_{0.6}$** |
|---|---|---|---|---|
| Application Example 1 | 2.30 | 0.10 | 1.0 | 15.6 steps |
| Comparative Example | 2.42 | 0.07 | 1.3 | 9.5 steps |

Notes:
*The image density and the fogging density were measured by Macbeth reflection densitometer RD-514 model [Red Filter]
**The number of steps of step tablets to obtain a density of 0.6.

It is evident from the results of Table 1 that according to the present invention, a photo-oxidizing agent having a higher sensitivity than the conventional photo-oxidizing agent was obtained.

This photosensitive sheet may suitably be employed as a proofing material capable of being fixed.

Application Examples 2 to 7

The operation was conducted in the same manner as in Application Example 1 except that the 2-(2-trifluoromethylphenyl)-4,5-bis(3,4-methylenedioxyphenyl)-imidazole dimer in the composition of Solution I was changed to a dimer having such a phenyl group at the 2-position as identified in Table 2. The results are shown in Table 2.

TABLE 2

| Example No. | Phenyl group at the 2-position | Image density | Fogging density | γ-value | Sensitivity $D_{0.6}$ |
|---|---|---|---|---|---|
| 2 | 2-Cl-C₆H₄– | 2.25 | 0.09 | 1.0 | 12 steps |
| 3 | 2,6-Cl₂-C₆H₃– | 2.34 | 0.08 | 1.1 | 14 steps |
| 4 | 2,4-(CH₃O)₂-C₆H₃– | 2.05 | 0.06 | 1.2 | 10 steps |
| 5 | 2,4-Cl₂-C₆H₃– | 2.40 | 0.09 | 1.0 | 13 steps |
| 6 | 2,5-Cl₂-C₆H₃– | 2.45 | 0.08 | 1.3 | 15 steps |
| 7 | 2-CH₃O-4-Cl-C₆H₃– | 2.30 | 0.09 | 1.0 | 14 steps |

We claim:

1. A 2,4,5-triphenylimidazole compound having the formula:

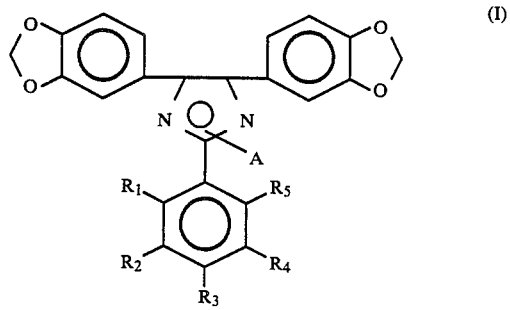

(I)

wherein each of $R_1$ to $R_5$ is a hydrogen atom, a $C_1$–$C_4$ alkyl group, a $C_1$–$C_4$ alkoxy group, a fluorine atom, a chlorine atom, a bromine atom, a trifluoromethyl group or a trichloromethyl group, and A is a group having the formula:

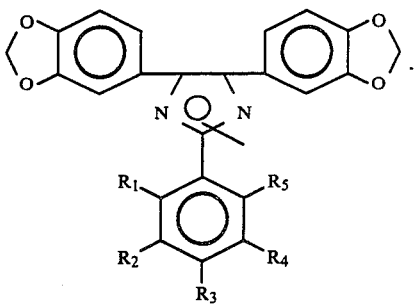

(II)

wherein $R_1$ to $R_5$ are as defined above.

2. The compound according to claim 1, which is a dimer of 2-(2-chlorophenyl)-4,5-bis(3,4-methylenedioxyphenyl)-imidazole.

3. The compound according to claim 1, which is a dimer of 2-(2,3-dichlorophenyl)-4,5-bis(3,4-methylenedioxyphenyl)-imidazole.

4. The compound according to claim 1, which is a dimer of 2-(2-trifluoromethylphenyl)-4,5-bis(3,4-methylenedioxyphenyl)-imidazole.

5. The compound according to claim 1, which is a dimer of 2-(2,4-dimethoxyphenyl)-4,5-bis(3,4-methylenedioxyphenyl)-imidazole.

6. The compound according to claim 1, which is a dimer of 2-(2,4-dichlorophenyl)-4,5-bis(3,4-methylenedioxyphenyl)-imidazole.

7. The compound according to claim 1, which is a dimer of 2-(2,6-dichlorophenyl)-4,5-bis(3,4-methylenedioxyphenyl)-imidazole.

8. The compound according to claim 1, which is a dimer of 2-(2-methoxy-5-chlorophenyl)-4,5-bis(3,4-methylenedioxyphenyl)-imidazole.

* * * * *